United States Patent
Hoster, Jr.

(10) Patent No.: US 6,425,399 B1
(45) Date of Patent: Jul. 30, 2002

(54) EMERGENCY INFLATABLE SPINAL SUPPORT DEVICE

(76) Inventor: William Hoster, Jr., 8477 S. Cornell Dr., Sandy, UT (US) 84094

( * ) Notice: Subject to any disclaimer, the term of this patent is extended or adjusted under 35 U.S.C. 154(b) by 0 days.

(21) Appl. No.: 09/664,045

(22) Filed: Sep. 5, 2000

Related U.S. Application Data (63) Continuation-in-part of application No. 08/912,554, filed on Aug. 18, 1997, now abandoned.

(51) Int. Cl.⁷ .................................................. A61F 5/37
(52) U.S. Cl. ........................ 128/869; 128/870; 5/627; 5/628
(58) Field of Search ................................ 128/869, 870; 5/628, 913, 625

(56) References Cited

U.S. PATENT DOCUMENTS

| | | |
|---|---|---|
| 1,576,211 A | 3/1926 | O'Kane |
| 3,689,945 A | 9/1972 | Laerdal |
| 3,745,998 A | 7/1973 | Rose |
| 4,024,861 A * | 5/1977 | Vincent ....................... 128/870 |
| 4,297,994 A | 11/1981 | Bashaw |
| 4,301,791 A * | 11/1981 | Franco, III .................. 128/870 |
| 4,466,145 A | 8/1984 | Jones et al. |
| 4,621,382 A | 11/1986 | Burriss et al. |
| 4,794,917 A | 1/1989 | O'Leary |
| 4,979,520 A | 12/1990 | Boone, Jr. et al. |
| 5,016,620 A | 5/1991 | Matthews |
| 5,070,559 A | 12/1991 | Pettifer |
| 5,088,137 A | 2/1992 | Rose |
| 5,121,756 A | 6/1992 | Koledin |
| 5,154,185 A | 10/1992 | Latimer et al. |
| 5,154,186 A | 10/1992 | Laurin et al. |
| 5,329,934 A | 7/1994 | Bowman |
| 5,433,741 A | 7/1995 | Truglio |
| 5,502,855 A | 4/1996 | Graebe |
| 5,560,059 A | 10/1996 | McQueen |
| 5,598,593 A | 2/1997 | Wolfe |
| 5,626,150 A * | 5/1997 | Johnson ....................... 128/870 |
| 5,826,583 A * | 10/1998 | Wood .......................... 128/870 |
| 6,138,306 A * | 10/2000 | Muhanna ..................... 128/870 |

* cited by examiner

*Primary Examiner*—Michael A. Brown
(74) *Attorney, Agent, or Firm*—Thorpe North & Western (57) ABSTRACT

An emergency inflatable spinal support device configured for use with a rigid backboard includes an inflatable bladder configured to be removable coupled to the backboard to conform to spaces between the backboard and the patient. Straps can be attached to the bladder to removable couple the bladder to the backboard. The inflatable bladder is expandable and collapsible between a first, uninflated configuration, and a second, inflated configuration. The bladder includes a lower surface to abut to the backboard, and an upper surface to conform to a patient's body. The upper surface may be concave when inflated. The bladder may include a plurality of elongated sections, including inner and outer sections with different heights. The bladder may be foldable and unfoldable between an initial, folded configuration, and a subsequent, unfolded configuration. A method for utilizing the bladder includes removably securing the bladder to the backboard. The patient is placed on the bladder, and the bladder inflated. The patient is secured to the backboard. After transportation, the patient is released and removed from the backboard. The bladder is deflated and removed from the backboard. The bladder is discarded and the cost of the bladder is billed to charged to the patient's bill.

28 Claims, 6 Drawing Sheets

EMERGENCY INFLATABLE SPINAL SUPPORT DEVICE

This application is a continuation-in-part of U.S. patent application Ser. No. 08/912,554, filed Aug. 18, 1997, now abandoned.

BACKGROUND OF THE INVENTION

1. The Field of the Invention.

The present invention relates generally to emergency medical support and comfort equipment. More particularly, the present invention relates to a emergency inflatable device for securing a patient's spinal region immediately following a trauma to that area of the body and during transport to a medical facility.

2. The Background Art.

It has long been known in the medical field that any movement of the spinal column following an accident or injury in which the spinal column is traumatized can paralyze the patient or even cause death. Accordingly, there are many apparatus and devices for supporting the spinal region of the body as a first treatment following a serious accident or trauma.

For example, devices known as backboards have been used and continue to be used by emergency medical personnel in virtually all first aid situations in which the spinal area is involved. These backboards are usually planar in shape and stiff in construction, typically being formed of wood, metal or hardened plastic, in order to provide a firm, yet transportable, support device. The use of a backboard entails generally the steps of laying the device next to the injured patient, gently moving the patient onto the backboard such that the backboard is contiguous with the patient's spinal region, if possible, and then securing the patient to the backboard in order to minimize or prevent movement during transport to a medical facility in an ambulance or other similar vehicle.

SUMMARY OF THE INVENTION

It has been recognized that it would be advantageous to develop an emergency spinal support device which provides comfort and support during transport to a medical facility to a patient suffering from spinal trauma. In addition, it has been recognized that it would be advantageous to develop a spinal support device which is easy, quick, inexpensive, and sanitary to use. In addition, it has been recognized that it would be advantageous to develop an effective and comfortable supplement to existing spinal support devices, such as backboards, in order to more efficiently transport spinal trauma patients to medical facilities.

The invention provides an emergency inflatable spinal support device configured for use with a rigid backboard. Preferably, the backboard is a standard, single, continuous backboard. The device includes an inflatable bladder configured to be removably coupled to the backboard. In addition, straps can be attached to the bladder to removable couple the bladder to the backboard.

In accordance with one aspect of the present invention, the inflatable bladder is expandable and collapsible between a first, uninflated configuration, and a second, inflated configuration. In the first, uninflated configuration the bladder is substantially flat. In the second, inflated configuration the bladder expands to fill a gap between the backboard and a patient's body.

In accordance with another aspect of the present invention, the bladder includes a lower surface to abut to the backboard, and an upper surface to conform to a patient's body. Preferably, the upper surface is concave when inflated. Preferably, the lower surface of the bladder is flat when coupled to the backboard.

In accordance with another aspect of the present invention, the bladder includes a plurality of elongated sections extending along a longitudinal axis of the bladder. The sections include inner sections located at a middle of the bladder, and outer sections located at a periphery of the bladder. Preferably, the outer sections have a height greater than a height of the inner sections. In addition, the bladder can include intermediate sections located between the inner and outer sections. The intermediate sections can have a height greater than the inner sections, but less than the outer sections.

In accordance with another aspect of the present invention, the bladder is foldable and unfoldable between initial and subsequent configurations. In the initial configuration the bladder is folded upon itself for storage. In the subsequent configuration the bladder is unfolded for use.

A method in accordance with the present invention includes providing a flat, rigid backboard, and an inflatable bladder. The bladder can be provided in an initial, folded configuration, and unfolded from the initial, folded configuration to a subsequent unfolded configuration which is substantially flat. The bladder is removably secured to the backboard. The patient is placed on the bladder, and the bladder inflated to conform to spaces between the backboard and the patient. The patient is secured to the backboard.

After transportation, the patient can be released and removed from the backboard. The bladder can be deflated and removed from the backboard. Preferably, the bladder is disposable and is discarded after use. The cost of the bladder can be charged to the patient's bill as a separate item.

Additional features and advantages of the invention will be set forth in the detailed description which follows, taken in conjunction with the accompanying drawing, which together illustrate by way of example, the features of the invention.

DETAILED DESCRIPTION

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

As illustrated in FIGS. 1–13, an emergency inflatable spinal support device, indicated generally at 10, is shown for supporting a patient 11, or spinal area of the patient, during transportation to a medical facility. Emergency medical teams or situations are examples fields which may benefit from use of such a device 10. The support device 10 generally includes an inflatable bladder 12 removably disposed on a rigid backboard 13.

The rigid backboard 13 preferably and advantageously can be a standard backboard as is commonly utilized by emergency medical teams, and/or commonly included with emergency medical equipment or carried by emergency medical vehicles. Utilizing a standard backboard 13 advantageously can reduce the cost of utilizing the present device 10 because a new or custom backboard is not required. In addition, utilizing the standard backboard 13 advantageously can be safer and more efficient because emergency medical personnel are already trained to use, and are familiar with, the standard backboard.

It will be appreciated that the patient 11, or the patient's body, is contoured and/or irregular, while the backboard 13 is rigid and flat. Thus, while placing the patient 11 on the backboard 13 may immobilize all or a portion of the patient 12, or the patient's spinal area, gaps 14 exist between the patient 11, or patient's body, and the backboard 13. The gaps 14 represent potential areas of movement for the patient 11 or patient's body with respect to the backboard 13, increasing the danger of additional injury, or aggravating injuries. In addition, it will be appreciated that the patient 11 is most likely injured, and that the backboard 13 is rigid and hard, which can result in discomfort and irritation to the patient 11.

The inflatable bladder 12 advantageously can be coupled to the backboard 13 to eliminate or reduce all or some of the gaps 14 between the patient 11 and the backboard 13, and to provide a cushion between the patient 11 and backboard 13. Thus, use of the inflatable bladder 12 advantageously may reduce the chances of further or aggravated injury, and may provide additional comfort. In addition, the bladder 12 advantageously can be removably attached to the backboard 13 as needed or desired. Thus, the bladder 12 does not interfere with the use of the backboard 13 in situations in which the bladder 12 is not needed or desired.

The bladder 12 can have a flexible exterior wall defining an interior cavity. Opposing and opposite top and bottom walls may be sealed about their perimeter to form the bladder. Advantageously, the bladder 12 can be constructed of a lightweight impervious material such as polyvinyl carbon, although it will be understood that other materials may be suitable.

Figures 7, 8, 9, 10:
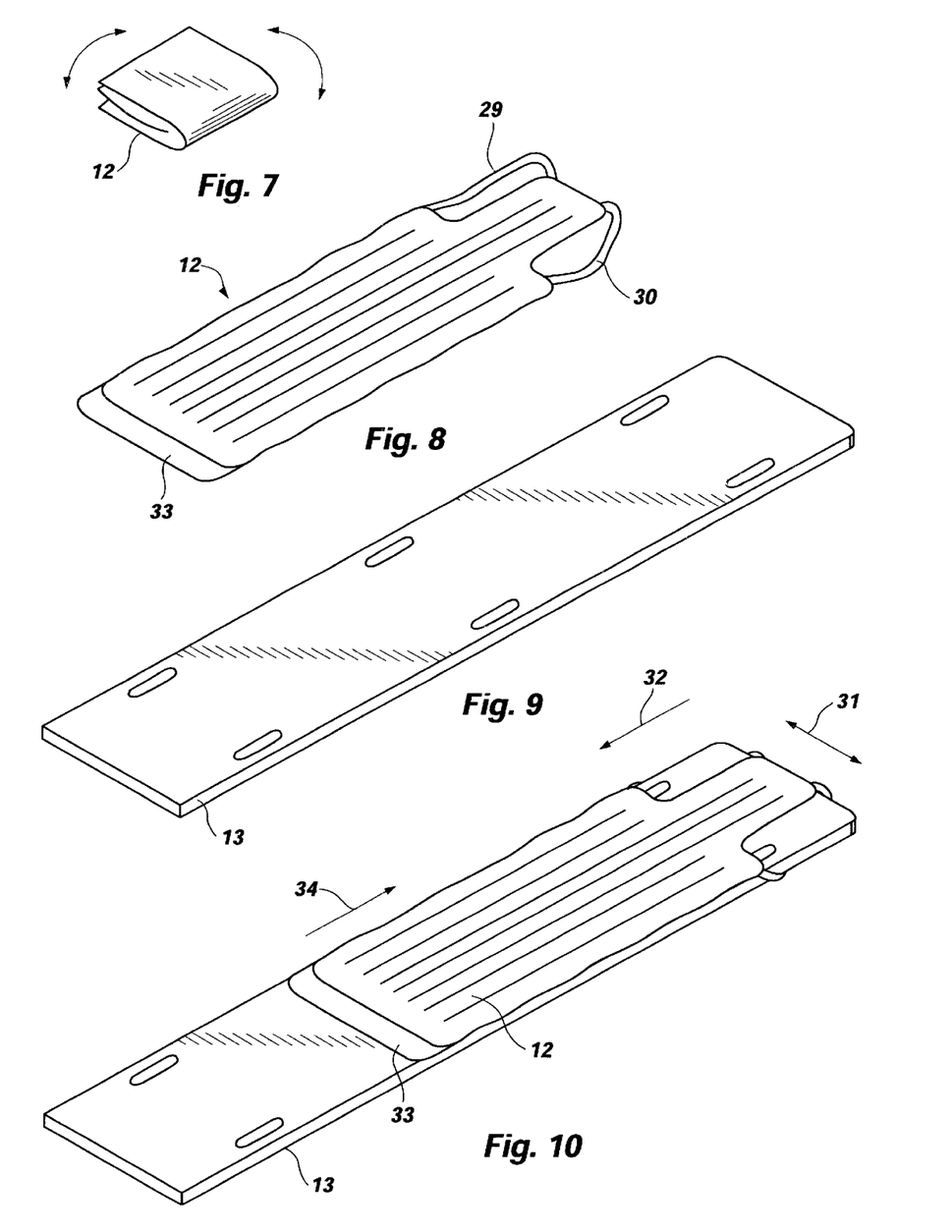
FIGS. 7–13 are schematic views showing a method of utilizing an emergency inflatable spinal support device in accordance with the present invention.
Figure 12:
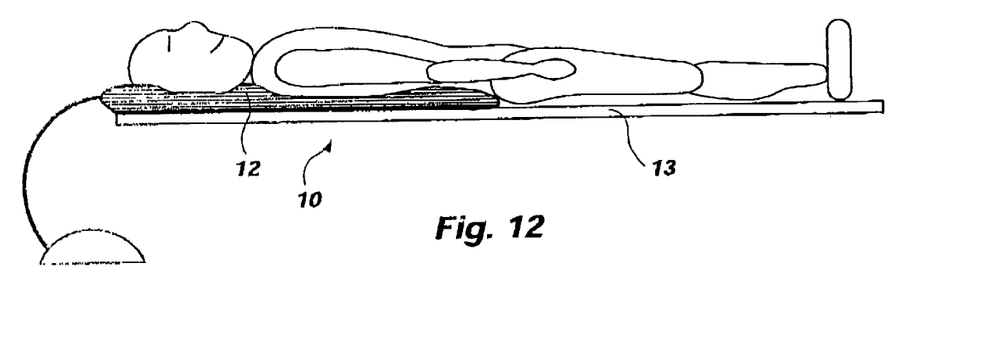
Figure 13:
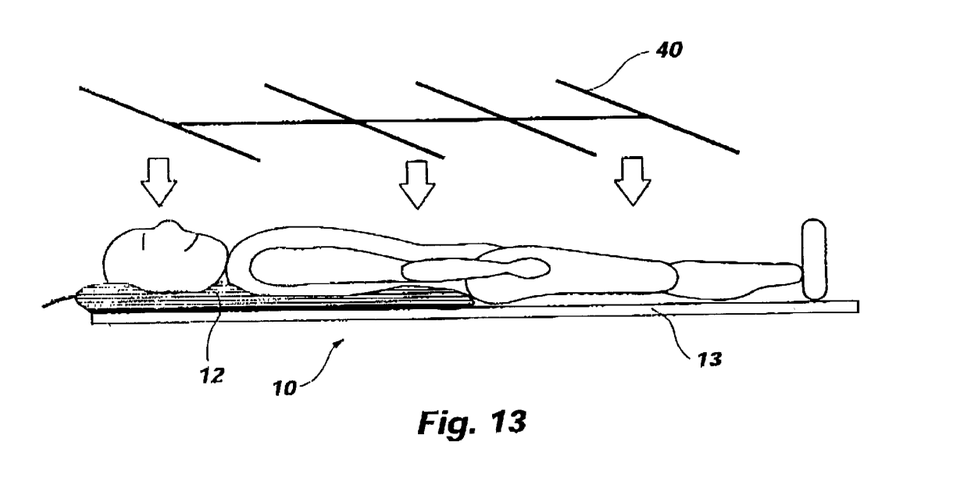

The inner cavity may be filled with a fluid or gas, and the flexible exterior wall may flex, such that the bladder 12 expands and collapses between first and second, or uninflated and inflated, configuration. In the first, uninflated configuration, the bladder 12 is substantially flat, as shown in FIG. 8, with the opposing top and bottom walls contacting or abutting one another. In the second, inflated configuration, the bladder 12 may be filled and expand to fill gaps 14 between the backboard 13 and the patient 11, as shown in FIG. 12. Filling the gaps 14 between the patient 11 and the backboard 13 eliminates or reduces the gaps 14 into which the patient 11, or the patient's body, may move during transportation, and thus can prevent further or aggravated injury.

The inflatable bladder 12 has a top face 18 and a an opposite bottom face 20. Preferably, the top face 18 is shaped to fit the overall shape of the patient 11, who, in use, is lying down atop the bladder 12. One skilled in the art will recognize that because there are many different shapes and sizes of body, there similarly may be several different shapes and sizes of bladder 12.

In addition, the top face 18 may be contoured to more closely match the patient 11, or patient's body, and/or to help retain the patient 11 on the backboard 13 and to provide a comfortable and secure feeling. The top face 18 of the bladder 12 can include a raised exterior edge 21 which generally follows the outline of the patient's body and is located directly outside the body's perimeter, and/or generally follows the perimeter of the backboard 13.

Figure 5:
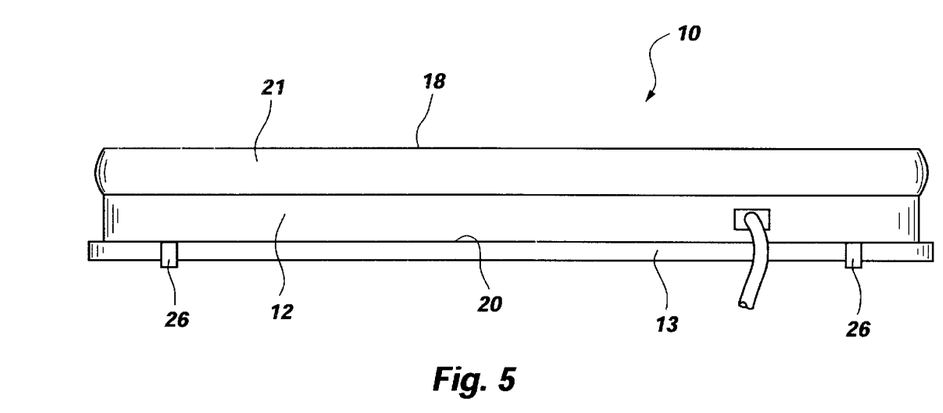
FIG. 5 is a side view of the device shown in FIG. 1, attached to a standard backboard.

The bottom face 20 of the bladder 12 is adapted to be mounted onto a standard backboard 13, as best illustrated in FIG. 5, and temporarily secured thereto. Thus, the bottom face 20 is generally flat to match the flat upper surface of the backboard 13.

Figure 1:
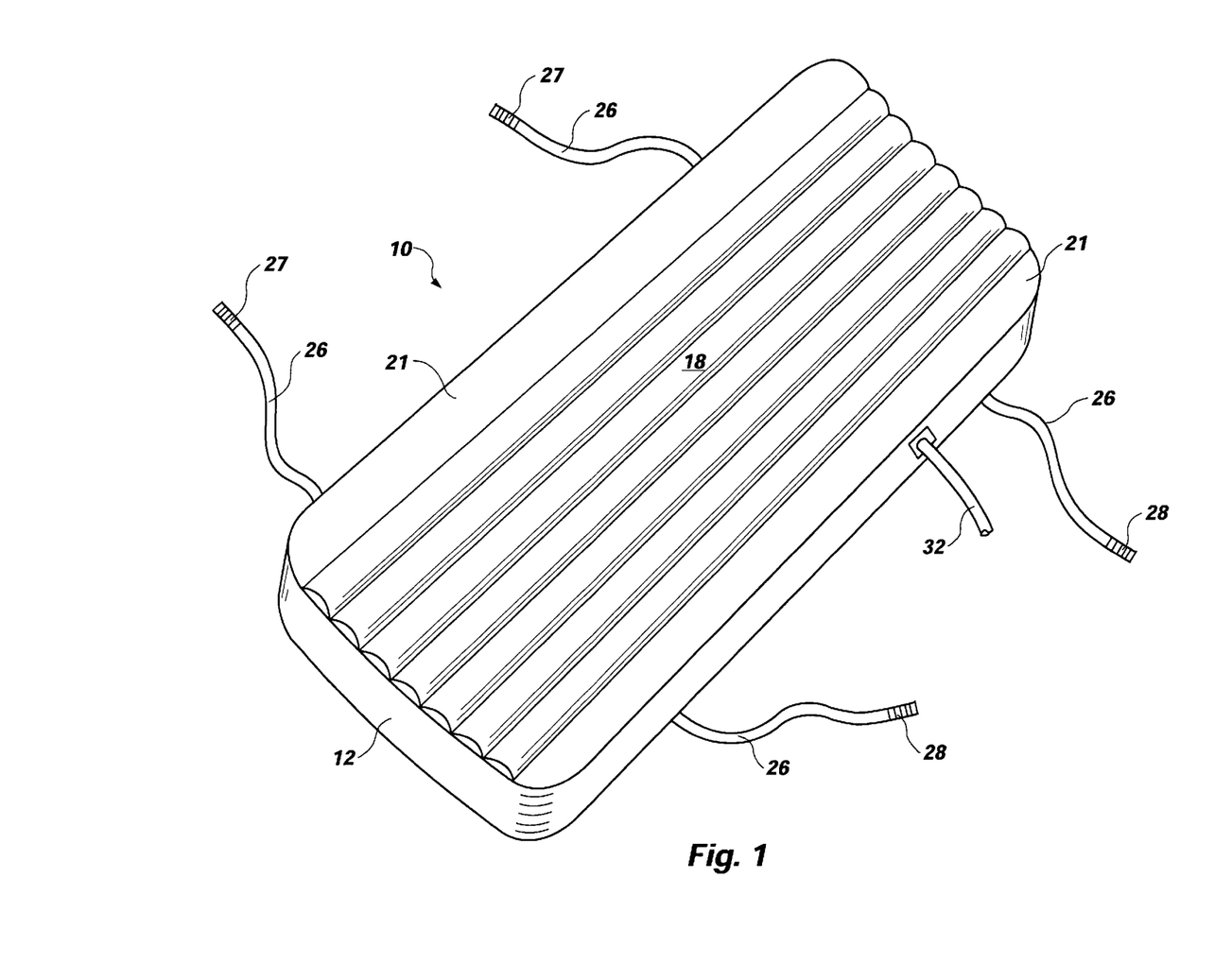
FIG. 1 is a perspective view of an emergency inflatable spinal support device in accordance with the present invention.
Figure 2:
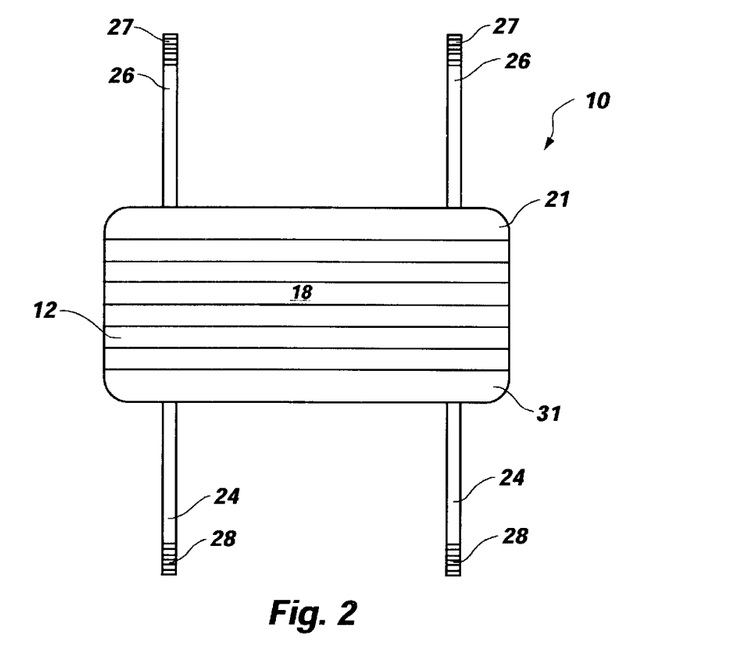
FIG. 2 is a top view of the device shown in FIG. 1.
Figure 3:
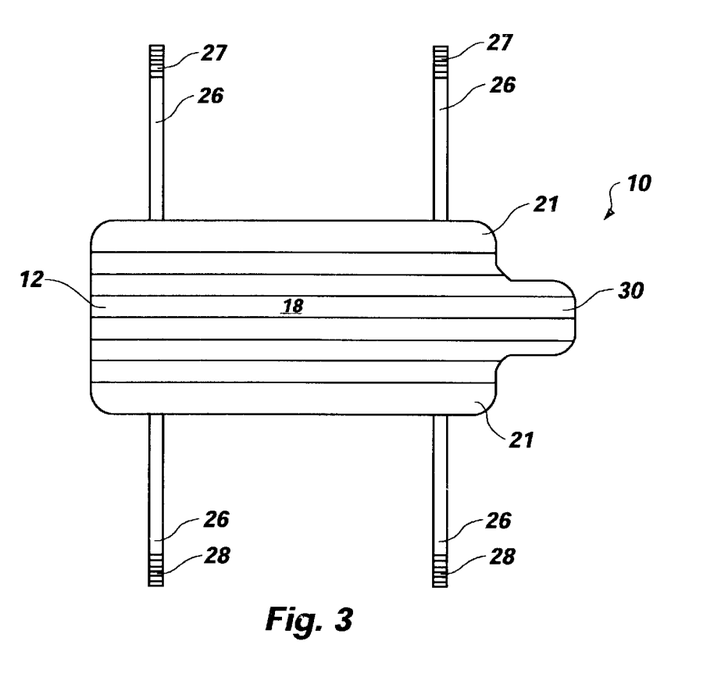
FIG. 3 is a top view of another emergency inflatable spinal support device in accordance with the present invention.
Figure 4:
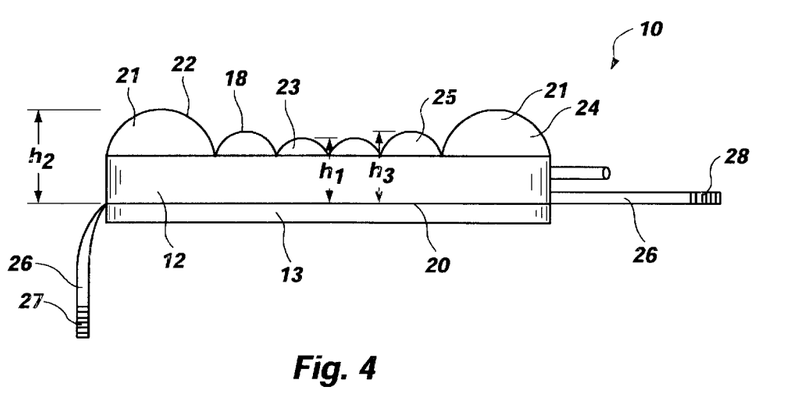
FIG. 4 is an end view of the device shown in FIG. 1.

Referring to FIG. 4, when the bladder 12 is inflated and attached to the backboard 13, the lower surface 20 remains flat, or abuts against the flat surface of the backboard 13, while the top surface 18 can be concave. The concave contour more closely matches the patient 11, or patient's body, and/or helps retain the patient 11 on the backboard 13. The bladder 12 can include a plurality of elongated sections 22 which extend along the length or longitudinal axis of the backboard 13 and/or bladder 12. The sections 22 can include inner sections 23 located at or near the middle of the bladder 12, and outer sections 24 located at or near the periphery of the bladder 12. The inner sections 23 preferably have a first height h1, such as from the bottom surface 20 or backboard 13 to the upper surface 18. Similarly, the outer sections 24 preferably have a second height h2 which is greater than the first height h1 of the inner sections 23. Furthermore, the sections 22 can include intermediate sections 25 between the inner and outer sections 23 and 24 with a third height h3 which is greater than the first height h1 of the inner sections 23, but less than the second height h2 of the outer sections 24. Thus, the upper surface 18 has a generally concave contour.

As stated above, the bladder 12 preferably and advantageously is removably secured to the backboard 13. A plurality of straps 26 may be attached to the bladder 12 for securing the bladder to the backboard 13. The straps 26 may be secured to the bottom face 20 of the bladder 12 in any number of ways. For example, the straps 26 may be heat pressed or sewn at one end to the bottom face 20.

The straps 26 may have free ends including fasteners for securing pairs of straps together about the backboard 13. For example, the free ends of the straps 26 can include either the engaging portion 27 or the receiving portion 28 of the traditional hook and loop type fasteners. The most common hook and loop type fasteners, and the sort preferred herein, are called Velcro fasteners and are available at any notions supply source. However, it is to be realized that any number of different fastening systems could be used within the purview of this invention. As indicated, the straps 14 engage the backboard 22 before being fastened together to secure the bladder 12 to the backboard 22. The straps may be made of a sturdy woven fabric or a plastic mesh, or any other material which is flexible, strong and unstretchable.

Alternatively, referring to FIGS. 8 and 10, a pair of straps 29 and 30 can be attached to opposite corners at one end of the bladder 12 to form a pair of loops. Each loop can extend around one of the opposite corners at an end of the backboard 13. The loops prevent or resist lateral movement, indicated by arrow 31, and longitudinal movement in one direction, indicated by arrow 32. The opposite end of the bladder 12 may be provided with an adhesive strip 33 which may be releasably adhered to the backboard 13 at an intermediate portion to prevent or resist lateral movement 31 and longitudinal movement 32 and 34, and to maintain the loops around the backboard 13.

Figure 6:
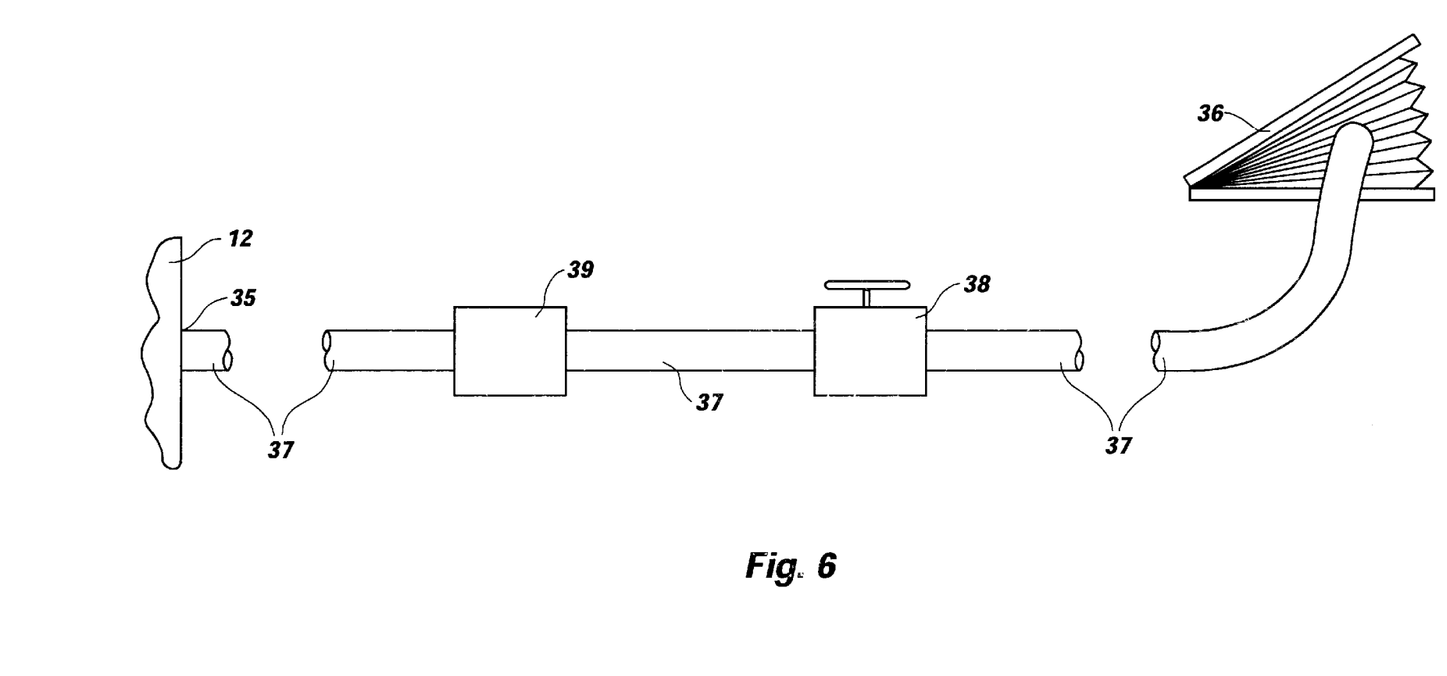
FIG. 6 is a partial schematic representation of the manner in which device of the present invention is inflated and deflated.

Referring now to FIG. 6, the bladder 12 may be provided with an opening 35 to provide fluid communication to the interior of the bladder 12. Preferably, the opening is located at the head end of the bladder 12. A pump 36, such as a foot pump, may be coupled in fluid communication with the bladder 12 via a flexible impervious hose 37. Thus, the operator can actuate the device 10 by repeatedly stepping on the foot pump 13, which forces air through the hose 37 and into the bladder 12 to force it to rise, thereby providing a comfortable cushion for the patient as he or she is taken to the hospital or other medical care facility. One skilled in the art will recognize that other inflation systems may be used to accomplish the function of the foot pump 36, such as $CO_2$ inflators, or gas or oxygen tanks.

A shut-off valve 38 and/or a pressure relief valve 39 may be coupled to the bladder 12, or hose 37. The shut-off valve 38 allows the operator to allow or disallow the ingress and egress of air into or out of the bladder 12, according to need. For example, when the desired pressure has been reached in the bladder 12 after filling it with air, the valve 38 may be actuated to prevent further ingress of air to increase the pressure or egress of air to decrease the pressure. Furthermore, the pressure relief valve 39 will prevent the overbuildup of pressure within the bladder 12 by releasing excess gas.

Referring to FIG. 7, the bladder 12 preferably is flexible, or formed of a flexible material, as stated above. Thus, the bladder can be folded and unfolded between a first, initial configuration, and a second, subsequent configuration. In the initial configuration, the bladder 12 may be folded upon itself, as shown in FIG. 7, for storage. The folded configuration of the bladder 12 preferably and advantageously is small, such that one or more bladders 12 may be easily stored with emergency medical equipment and/or vehicles. In addition, a protective wrapper (not shown) can be disposed around the folded bladder 12 to keep the bladder 12 clean and sanitary, and resist infection of the patient. In the subsequent configuration, the bladder 12 is unfolded for use, and is substantially flat.

In use, the backboard 13 and bladder 12 can be provided, as shown in FIGS. 8 and 9. The bladder 12 may be initially provided in a folded configuration, as shown in FIG. 7. Thus, the backboard 13 and bladder 12 can be stored separately, or unattached. The bladder 12 then can be unwrapped and unfolded (FIG. 8), if necessary. The bladder 12 then is placed on the backboard 13 so that the bladder is flat, as shown in FIG. 10, and releaseably secured. Straps 24, or 29 and 30, can be disposed around the backboard 13 and secured to attach the bladder 12 to the backboard 13. In addition, any adhesive strip 33 may have a protective backing layer removed and the strip 33 adhered to the backboard 13.

Figure 11:
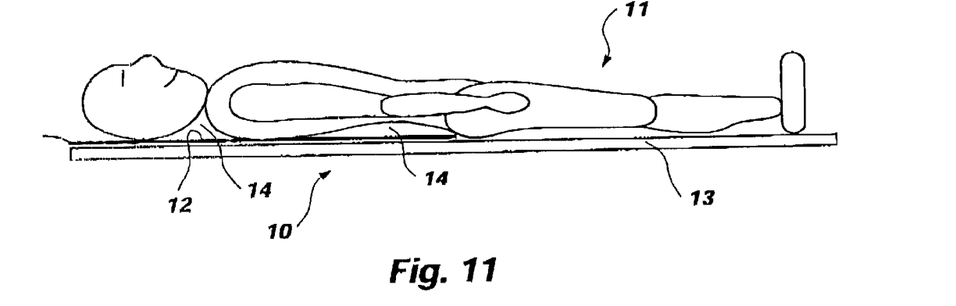

The patient 11 is placed on the bladder 12, and thus the backboard 13, as shown in FIG. 11. The top face 18 of the bladder 12 contacts the patient's posterior region, i.e., head, neck, back and/or legs. The bladder 12 preferably is uninflated, and flat, when the patient 11 is placed thereon. The bladder 12 is inflated to conform to the spaces or gaps 14 between the patient 11 and the backboard 13, as shown in FIG. 12. The foot pump 36 can be actuated to inflate the bladder 12 to a desired pressure, thereby providing a cushion of support for the patient. Advantageously, the shut-off valve 38 is then turned to the position in which no air is allowed out of or into the bladder 12, thereby maintaining a constant pressure within.

The patient 11 is secured to the backboard 13, such as with straps 40, or in any other appropriate manner. The bladder 12 preferably should be inflated prior to securing the patient 11 to the backboard 13 to prevent discomfort or injury.

After the patient 11 has been transported, the patient 11 can be released from the backboard 13, such as by releasing the straps 40, and removed from the backboard 13. The bladder 12 advantageously can be deflated and removed from the backboard 13. Preferably, the bladder 12 is discarded to prevent infection and the cost of sanitizing. As indicated above, the bladder 12 preferably has a simple design, and is formed of inexpensive materials, so that the bladder 12 may be disposable. In addition, the bladder 12 advantageously may be charged to the patient's bill as a separate item, much like other disposable medical supplies.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims.

What is claimed is:

1. An emergency inflatable spinal support device configured for use with a rigid backboard, comprising:
    a) an inflatable bladder configured to be removable coupled to the backboard; and
    b) straps attached to the bladder and extending therefrom to wrap around the backboard to removable couple the bladder to the backboard.

2. A device in accordance with claim 1, wherein the inflatable bladder is expandable and collapsible between:
    a) a first, uninflated configuration in which the bladder is substantially flat; and
    b) a second, inflated configuration in which the bladder expands configured to fill a gap between the backboard and a patient's body.

3. A device in accordance with claim 1, wherein the bladder includes a lower surface configured to abut to the backboard, and an upper surface configured to conform to a patient's body; and wherein the upper surface is concave when inflated.

4. A device in accordance with claim 3, wherein the lower surface of the bladder is flat when coupled to the backboard.

5. A device in accordance with claim 1, wherein the bladder includes a plurality of elongated sections extending along a longitudinal axis of the bladder and disposable on the backboard, the sections including inner sections located at a middle of the bladder, and outer sections located at a periphery of the bladder; and wherein the outer sections have a height greater than a height of the inner sections.

6. A device in accordance with claim 5, wherein the bladder further includes intermediate sections located between the inner and outer sections; and wherein the intermediate sections have a height greater than the inner sections, but less than the outer sections.

7. A device in accordance with claim 1, wherein the bladder is foldable and unfoldable between:
  a) an initial configuration in which the bladder is separate from the backboard and folded upon itself for storage; and
  b) a subsequent configuration in which the bladder is unfolded for use.

8. A device in accordance with claim 1, wherein the bladder further includes:
  a) a pair of straps attached to one end of the bladder to form a pair of loops each configured to extend around opposite side corners of the backboard; and
  b) an adhesive strip, disposed at another end of the bladder, configured to releasably adhere the bladder to an intermediate portion of the backboard.

9. A device in accordance with claim 1, further comprising a flat, rigid backboard.

10. A device in accordance with claim 1, wherein the straps form a loop extending around at least a portion of the backboard.

11. An emergency inflatable spinal support system, comprising:
  a) a flat, rigid backboard configured to rigidly secure a patient;
  b) an inflatable bladder, removably secured to the backboard; and
  c) at least one strap, attached to the inflatable bladder, removably wrapped around the backboard to removably secure the inflatable bladder to the backboard.

12. A system in accordance with claim 11, wherein the backboard includes opposite ends, opposite side corners at each end, and an intermediate portion between the ends; and wherein the bladder further includes:
  a) a pair of straps attached to the bladder to form a pair of loops each extending around one of the opposite side corners of the backboard; and
  b) an adhesive strip, disposed at the second end of the bladder, to releasably adhere the second end of the bladder to the intermediate portion of the backboard.

13. A system in accordance with claim 11, wherein the backboard is a single, integral, continuous backboard.

14. A system in accordance with claim 11, wherein the inflatable bladder is expandable and collapsible between:
  a) a first, uninflated configuration in which the bladder is substantially flat; and
  b) a second, inflated configuration in which the bladder expands configured to fill a gap between the backboard and a patient's body.

15. A system in accordance with claim 11, wherein the bladder includes a lower surface configured to abut to the backboard, and an upper surface configured to conform to a patient's body; and wherein the upper surface is concave when inflated.

16. A system in accordance with claim 15, wherein the lower surface of the bladder is flat when coupled to the backboard.

17. A system in accordance with claim 11, wherein the bladder includes a plurality of elongated sections extending along a longitudinal axis of the bladder and disposable on the backboard, the sections including inner sections located at a middle of the bladder, and outer sections located at a periphery of the bladder; and wherein the outer sections have a height greater than a height of the inner sections.

18. A system in accordance with claim 17, wherein the bladder further includes intermediate sections located between the inner and outer sections; and wherein the intermediate sections have a height greater than the inner sections, but less than the outer sections.

19. A system in accordance with claim 11, wherein the bladder is foldable and unfoldable between:
  a) an initial configuration in which the bladder is separate from the backboard and folded upon itself for storage; and
  b) a subsequent configuration in which the bladder is unfolded for use.

20. A system in accordance with claim 11, wherein the at least one strap forms a loop extending around at least a portion of the backboard.

21. A method for providing stabilization of a patient's spinal area during transportation, the method comprising the steps of:
  a) providing a flat, rigid backboard;
  b) providing an inflatable bladder;
  c) removably securing the bladder to the backboard;
  d) placing a patient on the bladder;
  e) inflating the bladder to conform to spaces between the backboard and the patient; and
  f) securing the patient to the backboard.

22. A method in accordance with claim 21, wherein the step of providing an inflatable bladder further includes the steps of:
  a) providing the bladder in an initial, folded configuration; and
  b) unfolding the bladder from the initial, folded configuration to a subsequent unfolded configuration which is substantially flat.

23. A method in accordance with claim 21, wherein the step of providing a backboard further includes providing a single, continuous backboard.

24. A method in accordance with claim 21, wherein the step of providing an inflatable bladder further includes providing a bladder with a pair of straps disposed at one end and an adhesive strip at the other end; and wherein the step of removably securing the bladder to the backboard includes looping the straps around two opposite corners of the backboard, and adhering the adhesive strip to the backboard.

25. A method in accordance with claim 21, wherein the step of providing an inflatable bladder further includes providing a bladder with a concave upper surface.

26. A method in accordance with claim 21, further comprising the steps of:

a) releasing the patient from the backboard;
b) removing the patient from the backboard;
c) deflating the bladder;
d) removing the bladder from the backboard; and
e) discarding the bladder.

27. A method in accordance with claim 21, further comprising the step of:

charging the cost of the bladder to the patient's bill as a separate item.

28. A method in accordance with claim 21, wherein:

a) the step of providing an inflatable bladder further includes providing a bladder with at least one strap; and
b) the step of removably securing the bladder to the backboard further includes wrapping the at least one strap around the backboard to form a loop around at least a portion of the backboard.

* * * * *